(12) United States Patent
Hammami et al.

(10) Patent No.: US 7,467,559 B2
(45) Date of Patent: Dec. 23, 2008

(54) APPARATUS AND METHODS FOR SAMPLE HANDLING AND RHEOLOGY ANALYSIS

(75) Inventors: Ahmed Hammami, Edmonton (CA); Terry Sopkow, Edmonton (CA); Shawn David Taylor, Edmonton (CA); Scott Jacobs, Edmonton (CA); Hussein Alboudwarej, Edmonton (CA)

(73) Assignee: Schlumberger Technology Corporation, Sugar Land, TX (US)

( * ) Notice: Subject to any disclaimer, the term of this patent is extended or adjusted under 35 U.S.C. 154(b) by 96 days.

(21) Appl. No.: 11/539,781

(22) Filed: Oct. 9, 2006

(65) Prior Publication Data
US 2008/0083268 A1   Apr. 10, 2008

(51) Int. Cl.
*G01N 1/16* (2006.01)
*G01N 35/10* (2006.01)

(52) U.S. Cl. ............... 73/863.82; 73/864.25; 73/864.31

(58) Field of Classification Search ............. 73/863.82, 73/864.25, 864.31, 864.32, 863.85, 863.86, 73/864, 866.5
See application file for complete search history.

(56) References Cited

U.S. PATENT DOCUMENTS

| | | | | |
|---|---|---|---|---|
| 2,934,959 | A * | 5/1960 | Johnson ................ | 73/863.82 |
| 4,061,036 | A * | 12/1977 | Legille .................. | 73/863.11 |
| 4,102,201 | A * | 7/1978 | Trine et al. ............ | 73/863.21 |
| 4,688,436 | A   | 8/1987 | Richon et al. | |
| 4,931,624 | A * | 6/1990 | Mellen, Sr. ........... | 219/497 |
| 4,949,940 | A * | 8/1990 | Weber .................. | 266/100 |
| 5,131,265 | A   | 7/1992 | Tobin et al. | |
| 5,146,796 | A * | 9/1992 | Mailliet et al. ......... | 73/866.5 |
| 5,263,376 | A * | 11/1993 | Sun ..................... | 73/864.31 |
| 5,315,863 | A   | 5/1994 | Cowper | |
| 5,546,791 | A   | 8/1996 | Meeten | |
| 6,023,962 | A   | 2/2000 | Wang et al. | |
| 6,517,779 | B1 * | 2/2003 | Luttermann et al. ........ | 422/100 |
| 6,629,451 | B1  | 10/2003 | Taylor | |
| 2004/0217059 | A1 | 11/2004 | Coville et al. | |
| 2004/0232075 | A1 | 11/2004 | Wells | |

OTHER PUBLICATIONS

Del Fabbro, M.; An Improved Technique for Studying Pleural Fluid Pressure and Composition in Rabbits; Experimental Physiology, 83 (1998) 435-448; Cambridge University Press.

(Continued)

*Primary Examiner*—Michael Cygan
(74) *Attorney, Agent, or Firm*—Jeffrey L. Wendt; Wayne I. Kanak (57) ABSTRACT

Apparatus and methods are described for isolating or manipulating a portion of a sample at non-ambient temperatures and pressures. One apparatus embodiment of the invention comprises a primary sample containment vessel defining a primary chamber, the vessel having a primary sample inlet and outlet; a secondary sample collection container defining a collection chamber fluidly connected to the primary containment vessel; and a sample probe comprising a distal end able to isolate a secondary sample in the primary chamber and transfer it to the collection chamber, the probe fluidly connected to the primary chamber via a seal allowing at least the distal end to be moved in 3-dimensions within the primary chamber. This abstract complies with rules requiring an abstract. It should not be used to limit the scope or meaning of the claims. 37 CFR 1.72(b).

10 Claims, 6 Drawing Sheets

OTHER PUBLICATIONS

Hammami, A., Ratulowski, J.; Precipitation and Deposition of Asphaltenes in Production Systems: A Flow Assurance Overview; Chapter 23; 2006.

Moran, K., Yeung, A., Masliyah, J.; Shape relaxation of an elongated viscous drop; Journal of Colloid and Interface Science 267 (2003) 483-493.

Shaw, J.M., Behar, E.; SLLV phase behavior and phase diagram transitions in asymmetric hydrocarbon fluids; Fluid Phase Equilibria 209 (2003) 185-206.

Tomos, A.D., Leigh, R.A.; The Pressure Probe: A Versatile Tool in Plant Cell Physiology; Annual Reviews, Plant Physiology, Plant Molecular Biology, 50 (1999) 447-72.

Yeung, A.K.C., Pelton, R.; Micromechanics: A New Approach to Studying the Strength and Breakup of Flocs; Journal of Colloid and Interface Science, 184 (1996) 579-585.

Zorgari, M., Jacobs, S., Ratulowski, J., Hammami, A.; Novel Organic Solids Deposition and Control Device for Live-Oils: Design and Applications; Energy & Fuels, (2006) 1656-1663.

* cited by examiner

APPARATUS AND METHODS FOR SAMPLE HANDLING AND RHEOLOGY ANALYSIS

BACKGROUND OF THE INVENTION

1. Field of Invention

The present invention relates generally to the field of fluid sample handling and/or interfacial rheology measurement at temperature and pressure conditions existing at the source of the sample, or at least temperatures different than ambient, including, but not limited to, reservoir hydrocarbon and aqueous based fluids, drilling muds, frac fluids, and the like having multiple phases (solids and liquid).

2. Related Art

Reservoir fluids often contain suspended particles under pressure and temperature conditions similar to those experienced in petroleum reservoirs and petroleum production systems. The particles may be in the form of a second liquid phase (hydrocarbon or aqueous based droplets) or in the form of a solid (organic or inorganic). The presence of these particles is related to the phase behavior of the petroleum fluid and thus, the nature and/or composition of these particles may change with changes in pressure, temperature, or overall composition. In order to improve understanding of the particle phase behavior, it is desirable to obtain samples of the suspended particles at defined pressure and temperature conditions for subsequent analytical characterization.

The phase behavior and physical properties of a reservoir fluid can be reasonably estimated through equation of state model(s) that have been tuned using experimental data. In such models, the fluid composition is normally described by lumped values (or pseudo components) that represent the average behavior of various portions within the fluid, such as C30+ compositions or SARA fractions. In the case of C30+ compositions, acceptable average critical values are assigned to each pseudo component so that the collection of pseudo components can be used in simulation packages to calculate the phase behavior and properties of each phase. While providing simplification of the simulation and analysis, such averaging can result in the loss of small, yet important variations in chemical composition that can affect large-scale behaviors. Examples of such behavior that have been observed in recent literature and internal studies are described below.

Multiple Liquid Phases: The formation of a second liquid phase in the form of micron sized droplets has been recently observed for some Gulf of Mexico fluids under near critical conditions. Recent studies have also demonstrated the ability of heavy and bituminous oils to form multiple liquid phases under various conditions, particularly when solvent has been added to the system (J. M. Shaw and E. Behar, Fluid Phase Equilibria, 209 (2003) 185-206). An asphaltene-rich liquid phase has also been observed in reservoirs where there is contact between the reservoir fluid and free gas and/or water phase. While it is known that this asphaltene-rich liquid forms a "tar-mat" in the reservoir, the compositional details or the mechanism of tar-mat formation are not known.

In all three of these examples, there is little known about the composition of the different liquid phases or their physical properties. Without this knowledge, it is impossible to develop the necessary equation of state (EOS) models or to be able to accurately simulate flow through porous media. While it is possible to experimentally determine the conditions at which different phases exist (see, for example, Shaw, J. M. et al., Fluid Phase Equilibria, 209 (2003) 185-206), it is not currently possible to isolate and sample the individual liquid phases under high pressure, high temperature conditions. Isolation of these phases is required to perform detailed composition and physical property analysis of each phase under various temperature and pressure conditions.

Asphaltene Precipitation and Deposition: Asphaltenes are heavy, highly aromatic molecules that often precipitate from oils due to reductions in pressure and/or temperature or blending with incompatible fluids (see A. Hammami and J. Ratulowski in: Asphaltenes, Heavy Oils and Petroleomics, Oliver C. Mullins, Eric Y. Sheu, Ahmed Hammami, Alan Marshall, Editors, Kluwer Academic Publications, PRECIPITATION AND DEPOSITION OF ASPHALTENES IN PRODUCTION SYSTEMS: A FLOW ASSURANCE OVERVIEW, Chapter 23, 2006). Asphaltenes also contain multiple polar compounds; including oxygen, nitrogen, and sulphur that make the asphaltene molecules surface active. This surface activity leads to asphaltene deposition on the walls of process equipment and transportation pipelines and allows asphaltene to participate in the stabilization of water-in-oil emulsions. The "strength" of the surface activity of individual asphaltene molecules is dependent on the variation in asphaltene composition. There is experimental evidence that a small, specific sub-fractions of the asphaltene is responsible for the deposits found on solid surfaces (see, for example, M. Zougari, S. Jacobs, A. Hammami, G. Broze, M. Flannery, J. Ratulowski and A. Stankiewicz, "Novel Organic Solid Deposition and Control Device for Live Oils: Design and Applications" Energy & Fuels, 20 (2006) 1656-1663).

Current experimental methods of studying asphaltenes in reservoir fluids involve the detection of solid precipitation in visual or non-visual pressure-volume-temperature (PVT) cells. A hydrocarbon-based fluid would be placed inside the PVT cell under pressure and temperature conditions similar to those experienced within a petroleum reservoir or in the petroleum production process. The pressure and/or temperature of the fluid would then be changed to induce the formation of a solid precipitate (e.g. asphaltene). Detection of solid formation in the hydrocarbon fluid may be done using near-infrared detectors, x-ray detection, or visual detection via a high pressure, high temperature microscopy method. These detection methods are limited to suspended particle detection only and cannot isolate or sample individual particles for subsequent analysis.

In the case of precipitated asphaltenes, high-temperature, high-pressure filtration may be used to collect the asphaltene aggregates and/or flocs. While commonly used, the high-pressure, high-temperature filtration process contains some potentially serious limitations to the analysis of asphaltene precipitate. The first and obvious limitation is that the floc size and amount of the recovered asphaltene depends on the pore size of the filter. Also, one must be very careful not to cause precipitated solids (wax and/or asphaltenes) to grate through the pores of the filter by creating too large of a pressure drop across the filter. Secondly, asphaltenes collected by filtration often contain trapped oil that contains dissolved organic solids (wax or asphaltene). There is a risk that these dissolved solids, particularly asphaltenes, can be precipitated during the removal of the trapped oil. The solids from the trapped oil would then be carried through with the filtered asphaltene precipitate, thus representing a "contaminant" that can affect subsequent analytical characterization. Finally, any measurements completed on the filtered solids (e.g., asphaltene) will only provide information about "average" asphaltene properties. The current protocols do not permit sampling and analysis of individual flocs and/or aggregates, an exercise that may reveal possible variations in chemical composition between the aggregates. With selective high-temperature, high-pressure micro-sampling, it may be possible to detect these compositional variations that contribute to both the surface activity and aggregation behavior of asphaltenes.

Few devices are disclosed in the patent literature for microsampling of process fluids. One such device is disclosed in U.S. published patent application Ser. No. 20040217059 A1 (Coville et al.), which discloses a method and apparatus for directly sampling a fluid for micro-filtration. In this device the fluid sample from a main container is filtered through a membrane before it is injected into a collecting chamber by a piercing instrument. The sample of interest in this micro-filtration device is the separated particulates, although the filtrate could also be sampled for analysis. The micro-filtration device is intended for mean filtration of a specimen to separate particles from about 0.01 micrometers to about 20 micrometers in size as measured in the longest dimension of the particle. A pressure source (air) is used to push the fluid through the membrane. Although this micro-filtration/sampling device could be used for any general micro-filtration, its intended use is for the filtration of blood samples. Again the device is not rated to the pressure and temperature range of interest in the micro-sampling of hydrocarbon reservoir fluids.

United States Published Patent application Ser. No. 20040232075 A1 (Wells), discloses a device and method to wash and concentrate (adjust composition of) solid particles from a suspension sample. A filter membrane is used to produce a permeate (fluid with no solids) flow low in solid particulates. A back-flushing mechanism was introduced to remove the solid particles from the membrane surface to recover filtration efficiency. The maximum allowable differential pressure across the membrane is 14.5 psi. As such the operating pressure was limited to atmospheric conditions. Maximum allowable fluid viscosity is 5 cP.

A micro-sampling device for collecting a pressurized liquid or gas sample for injection into a chromatography apparatus was disclosed in U.S. Pat. No. 4,688,436 (Richon et al). The device isolates a small volume of the reservoir fluid under the actual pressure and temperature before introducing it into a chromatograph carrier gas stream, thus carrying the total sample into the chromatograph. No measure of pressure and temperature ratings and sample volume is provided in the document.

Micro-sampling has been extensively used in the medical, biological, and botanical sciences to collect specimen (microsamples from living tissues and cells). One such instrument is the pressure probe described by Tomos et al., "The pressure probe: A versatile tool in plant cell physiology", Annual Review of Plant Physiology and Plant Molecular Biology, 50 (1999), 447-472, which has evolved from an instrument for measuring cell turgor and other water relation parameters into a device for sampling the content of individual higher plant cells in situ in the living plant. Obviously the so-called pressure probe is not suited for the pressure and temperature range of interest for hydrocarbon phase behavior. Another minimally invasive technique was described by del Fabbro, "An improved technique for studying pleural fluid pressure and composition in rabbits", Experimental Physiology, 83 (1998), 435-448, where capillary tubes were used to monitor the pleural fluid pressure and composition in live rabbits. The method included connecting polyethylene tubes to pleural space that provided means of measuring the pressure and collecting sub-samples from the pleural space.

Figure 1:
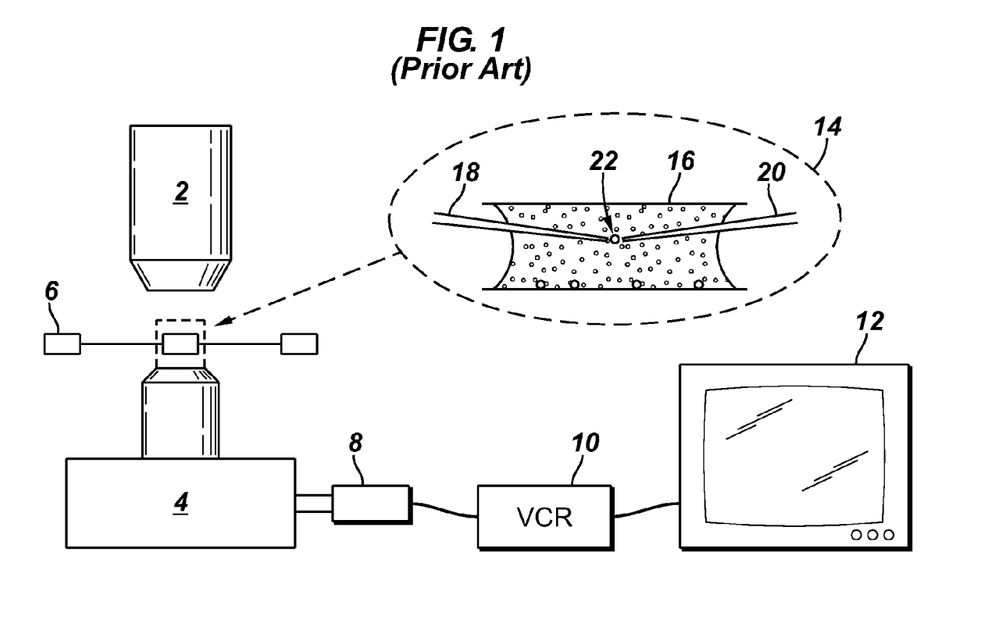
FIG. 1 is a schematic diagram of a prior art apparatus used to capture and manipulate individual droplets or cells within an aqueous or hydrocarbon media at atmospheric pressure and near ambient temperature conditions.

In addition to sample collection from living organisms, the selection and manipulation of suspended particles is common practice in biological and emulsion studies. A common technique utilizes glass micropipettes to capture and manipulate individual droplets or cells within an aqueous or hydrocarbon media at atmospheric pressure and near ambient temperature conditions (see for example Moran, "Micro-Mechanics of Emulsion Drops", PhD Thesis, University of Alberta, Edmonton, 2001). A schematic illustration is presented in FIG. 1. The technique involves placing a liquid containing suspend particles into a small glass container 16 open on two sides. Container 16 is then placed beneath a light source 2 such that individual particles may be observed, with the assistance of a microscope 4. As indicated in the inset view 14, one or more micropipettes 18, 20 are then inserted through the open sides of glass container 16 such that the tips of the micropipettes may be observed through microscope 4. Three-dimensional manipulators 6, 7 are then used to move the tips of the micropipettes and thus capture and manipulate suspended particles 22. A power source 8 powers light source 2, and may power a VCR 10 (which may record the images) and a monitor 12.

Glass micro-pipettes has also been used to investigate the interfacial rheology of liquid droplets (see for example Moran et al., "Shape relaxation of an elongated viscous drop", Journal of Colloid and Interface Science, 267 (2003), 483-493). In another application of the glass micro-pipettes (micro-cantilever technique), the strength and breakup of flocs (aggregates) have been studied (Yeung A. K. C and Pelton R., "Micromechanics: A New Approach to Studying the Strength and Breakup of Flocs", Journal of Colloids and Interface Science, 184 (1996), 579-585).

A long, but heretofore unmet, need exists in the art for apparatus and methods for isolating and/or measuring interfacial rheological properties of a portion of a sample at temperatures and pressures representing those existing at the source of the sample, or at least different than ambient laboratory conditions.

SUMMARY OF THE INVENTION

In accordance with the present invention, apparatus and methods for isolating and/or measuring interfacial rheological properties of a portion of a sample from a primary sample, under temperature and pressure conditions representative of the source of the primary sample (or at least different from ambient conditions), are described. The temperature and pressure conditions of the primary sample may be those of a petroleum reservoir or other hydrocarbon-bearing geologic formation, but the invention is not so limited. The primary sample may comprise any sample at elevated temperatures and pressures, including, but not limited to compositions comprising hydrocarbons (including sour hydrocarbons which may include hydrogen sulfide, mercaptans, and other sulfur-containing compounds), water, organic and/or inorganic solids, and may include micelles, macromolecules, globules, resins, asphaltenes, hydrocarbon and aqueous based fluids, drilling muds, frac fluids, and the like having multiple phases (solids and liquid). The primary sample composition may comprise one or more of each phase. Stated differently, a primary sample composition may comprise one or more liquid phases, one or more solid phases, and one or more gaseous phases.

One aspect of the invention are apparatus comprising:
(a) a primary sample containment vessel defining a primary chamber, the containment vessel having walls comprising materials capable of maintaining temperatures and pressures in the primary chamber at least different than ambient conditions, and in certain embodiments representative of a hydrocarbon-bearing reservoir, the container having a primary sample inlet and outlet;

(b) a secondary sample collection container defining a collection chamber fluidly connected to the primary containment vessel; and (c) a sample probe comprising a distal end able to isolate a secondary sample in the primary chamber and transfer the secondary sample to the collection chamber, the sample probe fluidly connected to the primary chamber via a seal between the containment vessel and the sample probe allowing 3-dimensional movement of at least the distal end of the sample probe within the primary chamber.

Apparatus within this aspect of the invention include those wherein the sample probe is selected from solid and hollow objects, and may be selected from a pointed object, a cup-shaped object, a catheter-like device comprising a sample grabber, and a pipette (for example a glass micropipette).

The primary sample containment vessel comprises at least one viewing port, wherein the viewing port may comprise any natural or synthetic material having suitable optical properties (substantially transparent) and mechanical properties able to withstand the desired temperature and pressure conditions. Suitable materials include sapphire and quartz. Certain embodiments of apparatus of the invention may have two or more viewing ports; one of the viewing ports may allow a camera or other charge couple device to visually access the primary chamber. Another viewing port may allow light from a light source to enter the primary chamber. In certain embodiments the viewing port or ports allow complete viewing of the distal end of the sample probe (and thus the secondary sample) from the moment the secondary sample is collected by the sample probe, through movement of the distal tip toward the sample container, through the time the secondary sample is placed into the collection chamber.

Apparatus within this aspect of the invention include those wherein the fluid connection between the primary sample chamber and secondary sample collection container is selected from mechanical barriers, interfacial barriers and any other form of barrier that would prevent the secondary sample collection chamber being contaminated by the non-sampled material in the primary sample chamber. An example of a mechanical barrier may be an elastomeric membrane; an example of an interfacial barrier may be an interface between two immiscible fluids.

Still other apparatus within this aspect of the invention include those wherein the secondary sample collection container includes a floating piston which functions to allow secondary samples and a solvent to fill a sub-chamber of the sample collection container, between the piston and the elastomeric membrane. The floating piston may be fluidly connected to a system allowing two-way flow of a motive fluid to effect and/or allow movement of the floating piston. The motive fluid may be gas or liquid.

Other apparatus of the invention include those wherein the seal between the sample probe and the primary containment vessel comprises a joint, for example a ball joint, having a substantially central passage therethrough, wherein the sample probe is positioned in the central passage. The joint may be an integral component of a pressurized sample probe container defining a sample probe chamber. The joint may allow the distal end of the sample probe to be moved in 3-dimensional space, including in translational movements (x, y, z) or by cylindrical movements (circular, radial and translational) or equivalent, inside of the primary chamber, and translational movement of the sample probe in and out of the secondary sample collection and sample probe chambers. The movement of the sample probe may be performed manually or automatically, for example, through computer control.

The sample probe chamber may be fluidly connected to a system allowing two-way flow of a solvent to effect pressurization of the sample probe chamber to a pressure substantially equal to that of the primary containment vessel. In certain embodiments the distal end of the sample probe is able to isolate secondary samples having a largest length dimension ranging from about 1 to about 100 micrometers, and in other embodiments of no larger than about 1 millimeter. Furthermore, despite the specific examples provided in the detailed description herein, the relative positions of the primary sample chamber, the secondary sample collection container, and sample probe (and sample probe container, if used) are not critical; inventive apparatus may be constructed in any manner that allows the sample probe to function to collect a secondary sample and move the secondary sample into the secondary sample collection container. Apparatus of this aspect of the invention may be used to capture and store micrometer-sized samples of solid particles or liquid droplets from petroleum fluids under high pressure and high temperature conditions, although apparatus within this aspect of the invention are not so limited.

Another aspect of the invention are apparatus for measuring interfacial rheology of particles in a primary sample at non-ambient conditions, one apparatus comprising:

(a) a primary sample containment vessel defining a primary chamber, the containment vessel having walls comprising materials capable of maintaining temperatures and pressures in the primary chamber at least different than ambient conditions, and in certain embodiments representative of a hydrocarbon-bearing reservoir, the container having a primary sample inlet and outlet; and (b) first and second sample probes each comprising a distal end able to manipulate one or more secondary samples in the primary chamber, the sample probes fluidly connected to the primary chamber via respective seals between the containment vessel and the sample probes allowing movement of the distal ends of the sample probes within the primary chamber in three dimensions.

Apparatus within this aspect of the invention share many, but not all, of the features of apparatus within the first aspect of the invention. The sample probes may or may not be positioned so that the distal ends are opposed, and each may comprise a glass micropipette as described in relation to the first aspect of the invention. Apparatus within the second aspect of the invention may find use for measuring values related to interfacial surface rheology (e.g., interfacial tension, interfacial viscosity, interfacial elasticity, and like interfacial properties), and/or rupture strength for solid flocs (aggregates).

Another aspect of the invention are methods of obtaining a secondary sample from a primary sample, one method comprising:

(a) loading a primary sample into a containment vessel defining a primary chamber, the containment vessel having walls comprising materials capable of maintaining temperatures and pressures in the primary chamber at least different than ambient conditions, and in certain embodiments representative of a hydrocarbon-bearing reservoir a hydrocarbon-bearing reservoir;

(b) isolating a secondary sample in the primary chamber using one or more sample probes; and (c) transferring the secondary sample to a secondary sample collection chamber using the one or more sample probes fluidly connected to the containment vessel using the one or more sample probes.

Methods within this aspect of the invention include those wherein the isolating and transferring steps comprise manipulating the one or more sample probes fluidly connected to the primary containment vessel through a joint, such as described in relation to the first aspect of the invention, such as a ball joint, allowing the sample probe to be moved in 3-dimensional space, including in translational movements (x, y, z) or by cylindrical movements (circular, radial and translational) or equivalent, inside of the primary chamber.

Yet another aspect of the invention are methods of manipulating one or more particles in a primary sample at non-ambient conditions, one method comprising:

(a) loading a primary sample comprising particles into a containment vessel defining a primary chamber, the containment vessel having walls comprising materials capable of maintaining temperatures and pressures in the primary chamber at least different than ambient conditions, and in certain embodiments representative of a hydrocarbon-bearing reservoir a hydrocarbon-bearing reservoir; and (b) manipulating a secondary sample comprising one or more particles in the primary chamber using one or more sample probes.

Methods within this aspect of the invention include measuring one or more interfacial rheological parameters of the one or more particles. Interfacial rheological parameters may include, but are not limited to, interfacial tension, interfacial viscosity, interfacial elasticity, rupture strength for solid flocs (aggregates), and the like. Manipulation of the one or more particles may be performed using two opposed micropipettes, although the invention is not so limited.

Apparatus and methods of the invention will become more apparent upon review of the detailed description of the invention and the claims that follow.

BRIEF DESCRIPTION OF THE DRAWINGS

The manner in which the objectives of the invention and other desirable characteristics may be obtained is explained in the following description and attached drawing in which:

FIG. 4 is a schematic diagram illustrating some of the movements a sample probe component of the embodiment of FIGS. 2 and 3 is capable of;

It is to be noted, however, that the appended drawings are not to scale and illustrate only typical embodiments of this invention, and are therefore not to be considered limiting of its scope, for the invention may admit to other equally effective embodiments.

DETAILED DESCRIPTION

In the following description, numerous details are set forth to provide an understanding of the present invention. However, it will be understood by those skilled in the art that the present invention may be practiced without these details and that numerous variations or modifications from the described embodiments may be possible.

Figure 2:
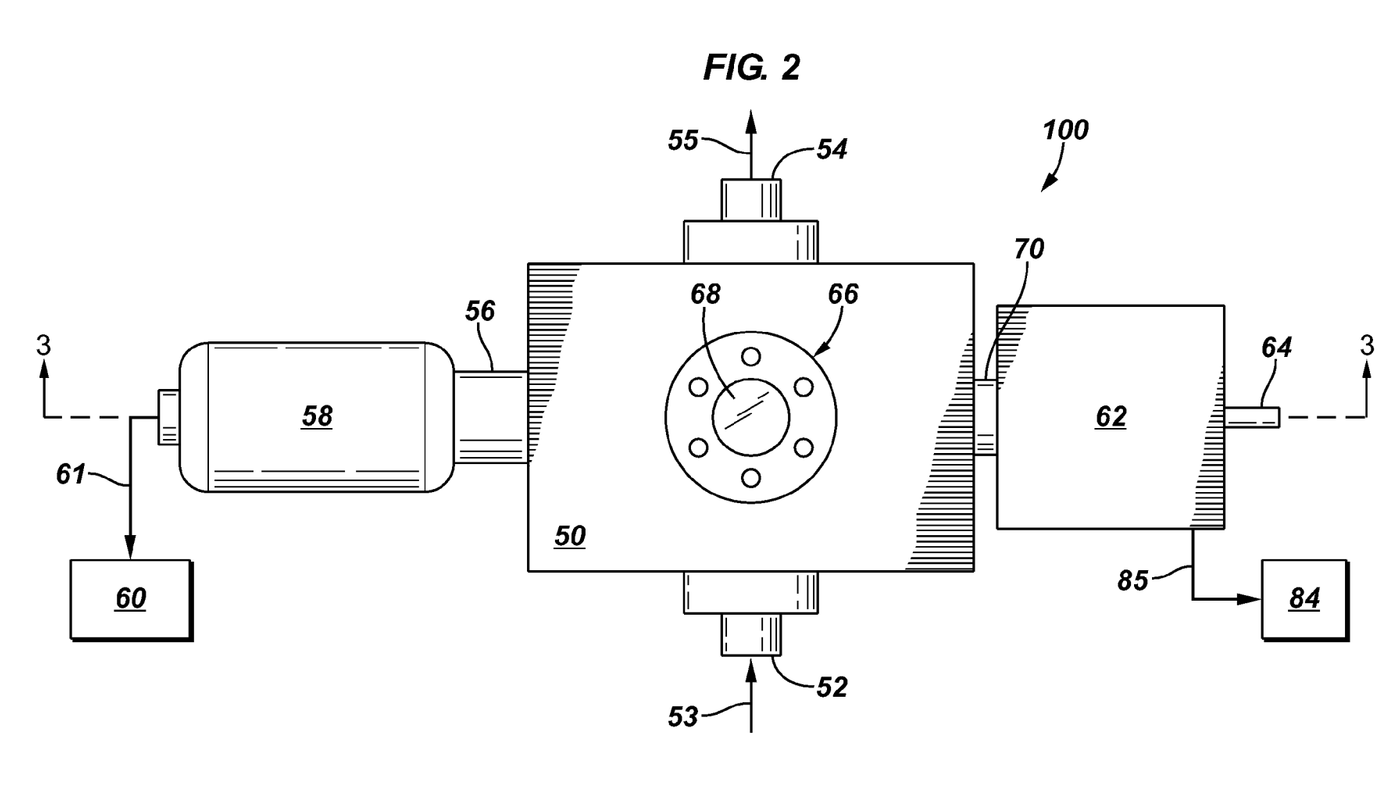
FIG. 2 is a schematic plan view of an apparatus within the invention that may be used to isolate secondary samples from a primary sample composition at non-ambient pressures and temperatures.
Figure 3:
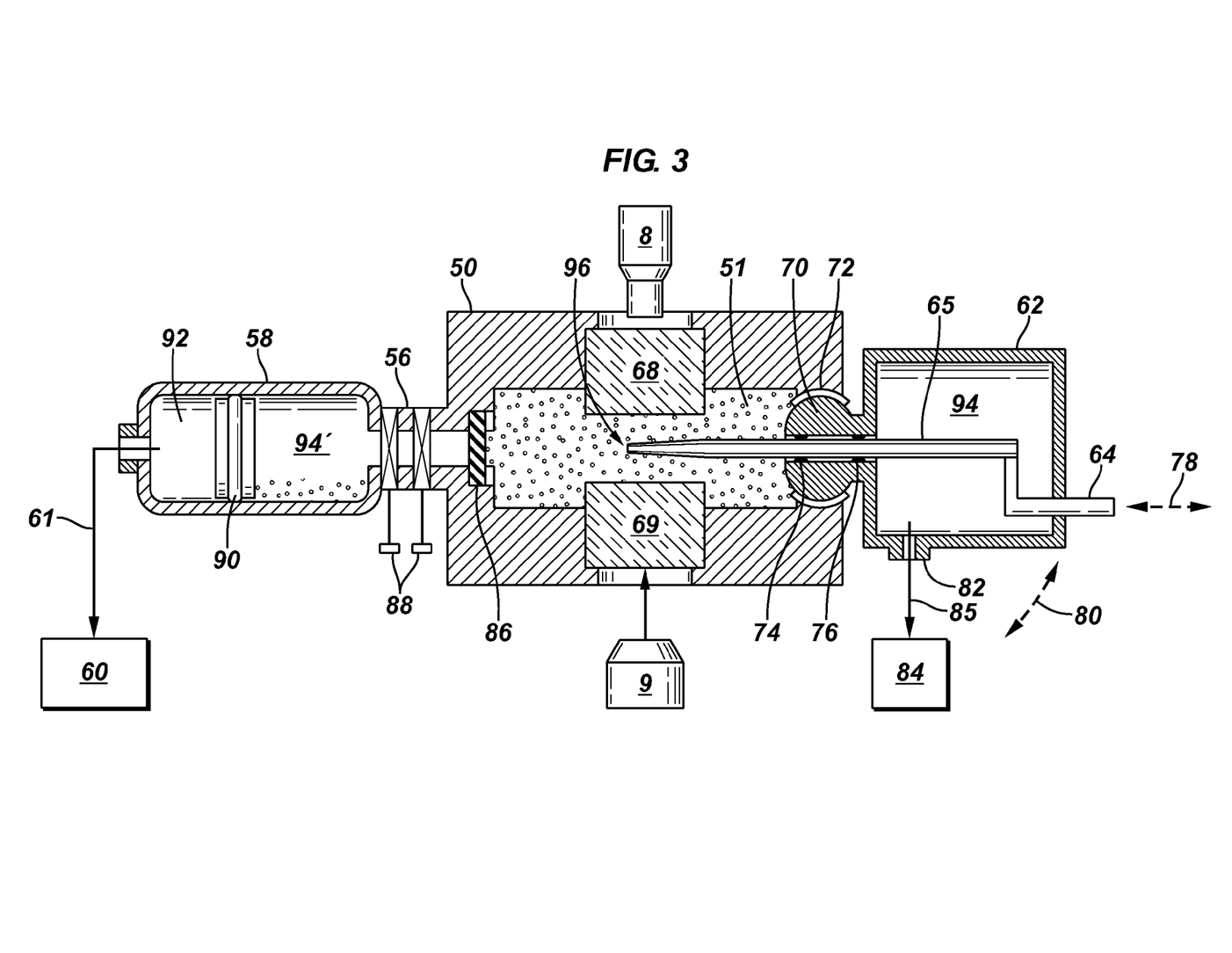
FIG. 3 is a schematic cross-sectional view of the apparatus of FIG. 2 taken along line 3-3.

FIGS. 2 and 3 illustrate schematic plan and cross-sectional views, respectively, of one apparatus embodiment 100 within the invention. It will be recognized by those skilled in the art that not all or the features in embodiment 100 may be necessary in all embodiments. Embodiment 100 comprises a primary sample containment vessel 50. Containment vessel 50 includes a primary sample inlet 52 and outlet 54, where a primary sample may enter and exit containment vessel 50, as illustrated by flow arrows 53 and 55. Containment vessel 50 comprises, in this embodiment, essentially a hollow metal block containing a top sapphire, quartz or other suitable material window 68 secured using a flange 66, a bottom window 69 also secured by a flange (not illustrated), and a more or less centrally located primary chamber 51, more easily viewed in FIG. 3. The primary sample inlet 52 and outlet 54 are illustrated connected perpendicular to the sapphire windows, but this is not strictly necessary to the invention. Primary sample inlet 52 and outlet 54 are used to isobarically and isothermally flow the reservoir fluid primary sample composition into primary chamber 51. A secondary sample collection vessel 58 is fluidly connected to containment vessel 50 through a port 56. A hydraulic pump 60 and line 61 supply and accept a hydraulic or other fluid to a sub-chamber internal of secondary sample collection vessel 58. A ball joint 70 fluidly connects containment vessel 50 with a micropipette sample vessel 62 in this embodiment. A manipulating handle is illustrated at 64 for manipulating a micropipette 65. A solvent pump 84 and line 85 are fluidly connected to micropipette sample vessel 62, whose operation in this embodiment will become apparent during the discussion of FIG. 3.

Referring more specifically now to FIG. 3, which is a cross-sectional view along the line 3-3 of embodiment 100 of FIG. 2, note that light from a light source 9 may be passed through bottom window 69, allowing the primary sample composition inside primary chamber 51 to be illuminated. Light source 9 may emit white light, laser light, polarized light or light of any single or combination of wavelengths. A color CCD camera 8 equipped with a high magnification lens may be positioned above top window 68 to allow for microscopic images of the fluid in primary chamber 51 to be captured in real-time. An opening through joint 70 allows micropipette 65 to access the primary sample composition within primary sample chamber 51. Micropipette 65 is sealed in a through passage of ball joint 70 by seals 74 and 76, but micropipette 65 is able to slide or otherwise move through seals 74 and 76. Port 56 provides an opening and serves as a fluid passage to a sub-chamber 94' in secondary sample collection vessel 58, where secondary samples (for example, particles) isolated from the primary sample are stored, along with a solvent in this embodiment. All of the openings in and out of containment vessel 50 comprise appropriate seals to ensure that the primary sample composition, same as a reservoir fluid, can be safely maintained under high-pressure, high-temperature conditions within primary sample chamber 51. Pressure inside primary sample chamber 51 is controlled using high-pressure positive displacement pumps (not illustrated) connected to the various flow lines, for example primary sample inlet 52 and outlet 54 (FIG. 2).

Figure 4:
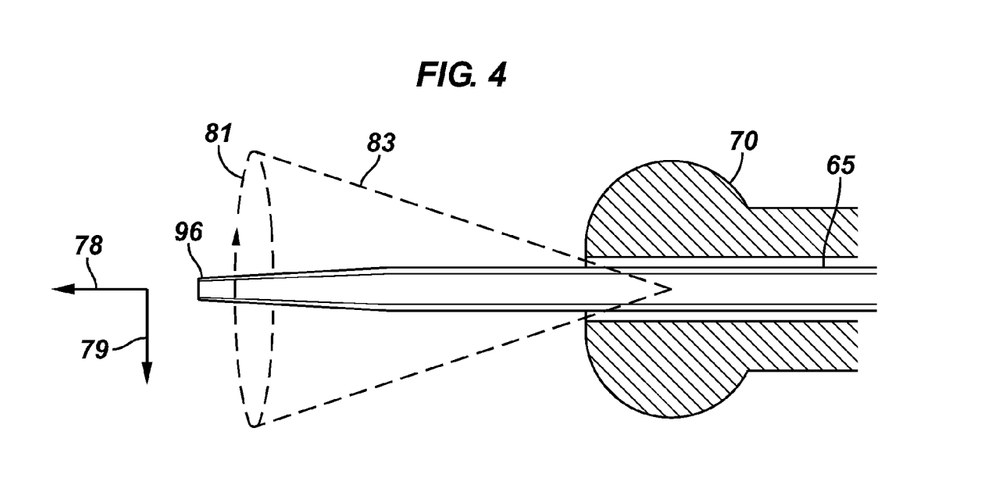

In embodiment 100, the sample probe is a micropipette sampling tool 65, although other sample probes may be useful in practicing the invention, as further discussed herein. When a micropipette sample probe is used, it comprises a hollow tube open on both ends, where one end, referred to herein as the distal end 96, may be tapered to a tip diameter on the order of tens of micrometers. During use, tapered distal end 96 is located in primary chamber 51 with the tapered distal end 96 located in the space between sapphire windows 68 and 69 so that it can be viewed on the CCD camera. The middle portion of micropipette 65 extends through the center of joint 70, which is also sealed as illustrated at 72, and into a pressure chamber 94 defined by micropipette sample vessel 62. Micropipette 65 may be formed from a single piece of metal, plastic, or glass, or may be formed from a composite of materials, such as a glass tube encased in metal or two metal tubes in a pipe-in-pipe configuration. Dynamic seals 74 and 76 surrounding the micropipette in joint 70 act to (i) isolate chamber 94 from primary chamber 51, and (ii) allow limited 3-dimensional movement of micropipette 65, as indicated by double-headed arrows 78, 80. Micropipette sample vessel 62 may be formed from a single piece of metal, including joint 70, which may be a ball joint. The ball joint design allows movement of micropipette tip 96 in 3-dimensions as indicated by double-headed arrow 80, where the center of the ball joint acts as the pivot point for radial and circular movement. The radial and circular movements allow micropipette distal end 96 to cover a cone shaped space 83, as illustrated schematically in FIG. 4. The combined translational 78, radial 79, and circular 81 movements allow for complete three-dimensional movement of at least the micropipette distal end 96 within primary chamber 51. Computer operated hydraulic or step gear motors (not illustrated) may be used to control the movement of micropipette distal end 96. A fitting 82 provides a connection between a solvent pump 84, a solvent supply line 85, and sample vessel 62. The ball mounted micropipette chamber 94 may be filled with a carefully selected solvent during operation and the pressure of ball mounted micropipette chamber 94 is balanced with the pressure in primary chamber 51.

Solvents useful in the invention may be selected from water, organic chemicals, and mixtures thereof, and may include inorganic ingredients. The composition is highly dependent on the particular pressure, temperature, and secondary sample to be isolated. As stated in the background section, reservoir fluids often contain suspended particles under pressure and temperature conditions similar to those experienced in petroleum reservoirs and petroleum production systems. The particles may be in the form of a second liquid phase (hydrocarbon or aqueous based) or in the form of a solid (organic or inorganic). The presence of these particles is related to the phase behavior of the petroleum fluid and thus, the nature and/or composition of these particles may change with changes in pressure, temperature, or overall composition. In order to improve understanding of the particle phase behavior, it is desirable to obtain samples of the suspended particles at defined pressure and temperature conditions for subsequent analytical characterization. The solvent is selected based on these principles.

Sample collection vessel 58 may be a vessel that is relatively small in volume compared with primary containment vessel 50, and is generally manufactured using the same or similar high-temperature, high-pressure corrosion resistant materials as containment vessel 50. Sample collection vessel 58 may be shaped as a cylinder, although this is not a requirement. An internal floating piston 90 acts to isolate a sub-chamber 92 filled with hydraulic fluid supplied from a positive displacement pump 60 and line 61, and a second sub-chamber 94' filled with the same solvent that is in sample vessel 62 (i.e. the same solvent used in pipette sample chamber 94). Sub-chamber 94' and the solvent therein are separated from primary sample composition in primary sample chamber 51 by a rubber membrane or fluid interface or interface of any kind or plug 86. The pressure of solvent in sub-chamber 94' is substantially balanced with that of the pressure in primary sample chamber 51.

In certain embodiments, the entire apparatus may be temperature controlled. Sources of temperature control include liquid baths, liquid jackets, peltier devices, convection gas baths, and the like. For example, a convection air bath may be employed to control the temperature in the entire apparatus to within ±5° C., and in certain embodiments within ±0.5° C. If vibration is to be minimized, apparatus of the invention may be isolated from its surrounding to minimize vibration of the apparatus.

In operation of apparatus embodiment 100 of the invention, primary sample chamber 51 will contain a fluid that is subjected to pressure and temperature conditions where either solid particles (e.g. wax or asphaltene) or droplets of a second liquid phase will be formed. An operator will be able to directly observe such micrometer-sized particles as well as the tip 96 of micropipette 65. The tip 96 of micropipette 65 will then be moved adjacent to a target particle and a slight relative suction draws the particle just inside tip 96, as illustrated in FIG. 3. Once captured, the particle will be placed inside sub-chamber 94' of sample collection vessel 58 by pushing tip 96 of micropipette 65 through a barrier such as an elastomeric membrane 86, or liquid interface between two immiscible liquids. With tip 96 inside sub-chamber 94', the particle is then displaced from micropipette 65. Multiple particle samples can be obtained by removing tip 96 from sub-chamber 94', positioning tip 96 adjacent to the next target particle, and repeating the capture/storage process. Once the sampling is complete, sample collection vessel 58 is isolated and removed from the apparatus and the sample collected for subsequent analytical characterization.

The minimum size or amount of secondary sample collected is determined by the minimum sample requirement for the specific analytical method of choice. Some of the currently available compositional analysis techniques only require nano-grams of material for proper analysis. Depending on the size of collected solid particles and/or liquid droplets and their density, multiple secondary sample collections may be required to collect enough material for analysis. For these and other reasons, secondary sample collection using apparatus and methods of the invention may be automated.

Primary sample compositions from which secondary samples may be collected may be gaseous, liquid, supercritical, and any combination thereof. The primary sample may comprise any sample at elevated temperatures and pressures, including, but not limited to compositions comprising hydrocarbons (including sour hydrocarbons which may include hydrogen sulfide, mercaptans, and other sulfur-containing compounds), water, organic and/or inorganic solids, and may include micelles, macromolecules, globules, resins, asphaltenes, hydrocarbon and aqueous based fluids, drilling muds, frac fluids, and the like having multiple phases (solids and liquid). The primary sample composition may comprise one or more of each phase. The term "reservoir" may include hydrocarbon deposits accessible by one or more wellbores. A "wellbore" includes cased, cased and cemented, or open-hole wellbores, and may be any type of well, including, but not limited to, a producing well, a non-producing well, an experimental well, an exploratory well, and the like. Wellbores may be vertical, horizontal, any angle between vertical and horizontal, diverted or non-diverted, and combinations thereof, for example a vertical well with a non-vertical component. The phrase "high temperature, high pressure" means any temperature and pressure conditions that are above atmospheric pressure and above 20° C.

Figure 5:
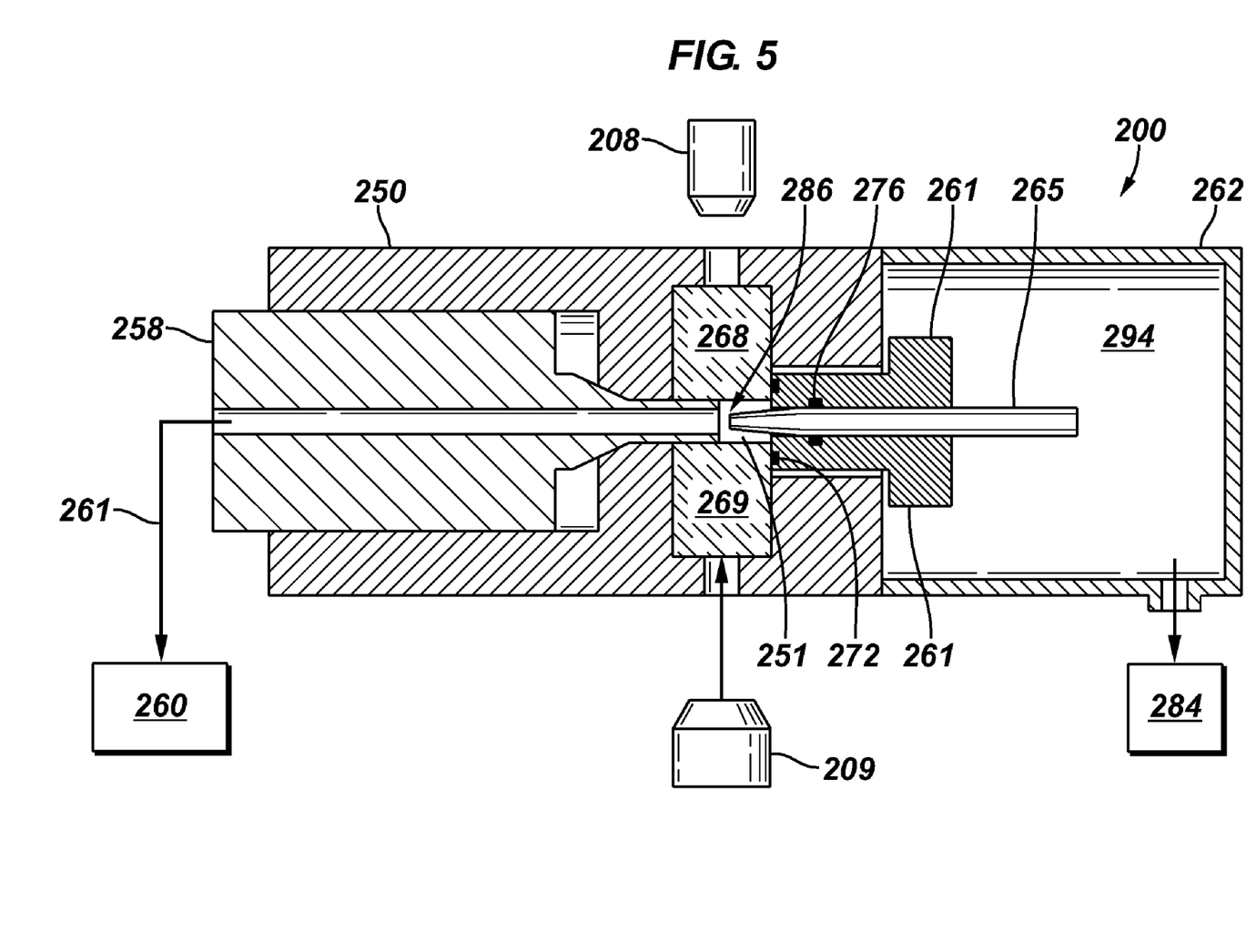
FIG. 5 is a schematic cross-sectional view of another apparatus within the invention similar to the view of FIG. 3.

FIG. 5 is a schematic cross-sectional view of another apparatus embodiment 200 within the invention, suitable for isolating secondary samples from a primary sample. Embodiment 200 includes a body 250 forming a primary sample chamber 251 (inlet and outlet are similar to those of embodiment 100 discussed above and are not illustrated) along with sapphire windows 268 and 269. As illustrated in this embodiment, note that a sample isolated by distal end 286 of sample probe 265 is viewable by a microscope 208 (with the help of light source 209) the entire time it is present in primary sample chamber 251 until deposited in secondary sample chamber 294' of secondary sample container 258. As in previous embodiment of the invention, a line 261 connects chamber 294' to a hydraulic pump 260. A hydraulic chamber 294 formed inside a sample probe containment vessel 262 is also connected to a hydraulic pump 284. Apparatus embodiment 200 differs from apparatus embodiment 100 in the operation of sample probe 265. In embodiment 200, sample probe 265 is supported in an adjustment block 261, which has a central passage through which the sample probe is inserted into and retracted from primary sample chamber 251 for the purpose of isolating secondary samples. Seals 272 and 276 prevent hydraulic fluid in chamber 294 from entering primary sample chamber 251 and vice versa, and allows sample probe 265, and thus distal end 286, to move in translational X-Y-Z directions, as indicated by the coordinate reference arrows.

Figure 6:
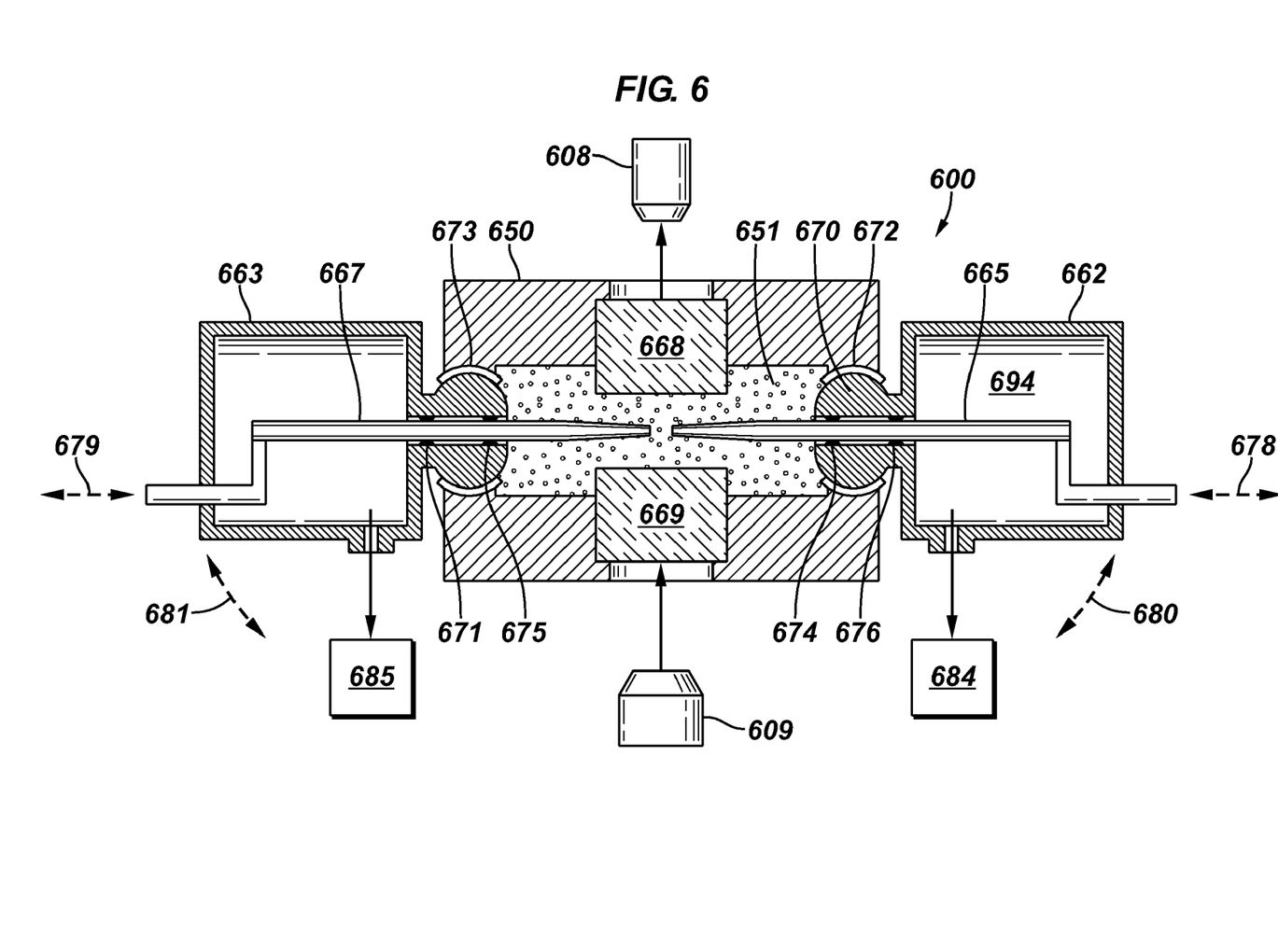
FIG. 6 is a schematic cross section of an apparatus of the invention that may be used to study rheological properties of particles and flocs.
Figure 7:
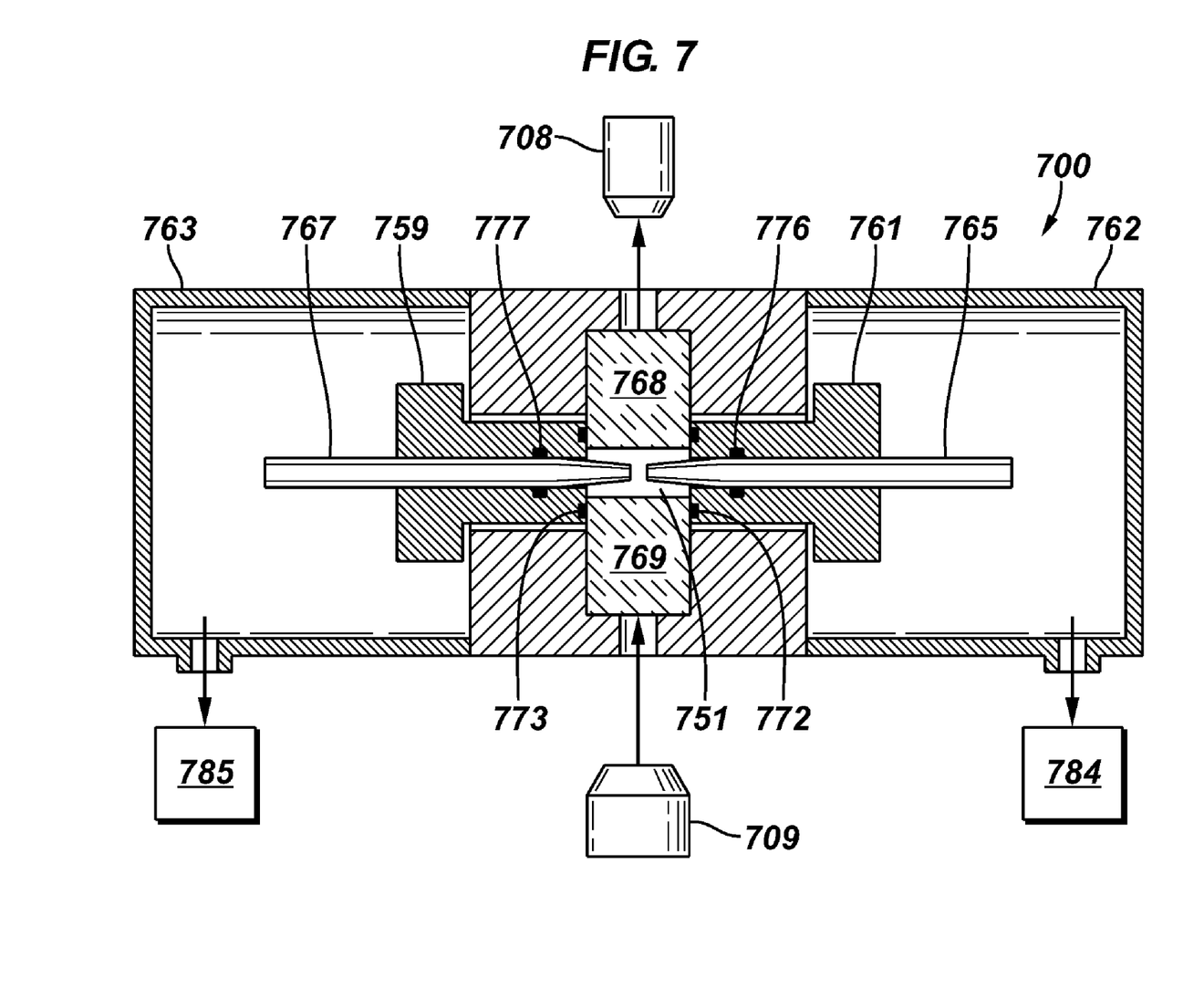
FIG. 7 is a schematic cross section of another apparatus of the invention that may be used to study rheological properties of particles and flocs.

FIGS. 6 and 7 are schematic cross-sections of apparatus embodiments 600 and 700, respectively, of the invention that may be used to study rheological properties of particles and flocs. Referring first to FIG. 6, embodiment 600 includes a primary sample containment vessel 650, the internal surfaces of which in part define a primary sample chamber 651. Sapphire windows 668 and 669 also in part define primary sample chamber 651. Embodiment 600 further comprises a first ball joint 670 fluidly connecting containment vessel 650 with a first micropipette sample vessel 662 in this embodiment. A first manipulating handle is illustrated at 664 for manipulating a first micropipette 665. A solvent pump 684 and line 685 are fluidly connected to first micropipette sample vessel 662, whose operation in this embodiment is essentially the same as described above with respect to embodiment 100 illustrated in FIG. 3. Light from a light source 609 may be passed through bottom window 669, allowing the primary sample composition inside primary chamber 651 to be illuminated. Light source 609 may emit white light, laser light, polarized light or light of any single or combination of wavelengths. A color CCD camera 608 equipped with a high magnification lens may be positioned above top window 668 to allow for microscopic images of the fluid and isolated particles in primary chamber 651 to be captured in real-time. An opening through first ball joint 670 allows first micropipette 665 to access the primary sample composition within primary sample chamber 651. First micropipette 665 is sealed in a through passage of first ball joint 670 by seals 674 and 676, but first micropipette 665 is able to slide or otherwise move through seals 674 and 676. In similar manner, embodiment 600 further comprises a second ball joint 671 fluidly connecting containment vessel 650 with a second micropipette sample vessel 663 in this embodiment. A second manipulating handle is illustrated at 664' for manipulating a second micropipette 667. A solvent pump 684' and line 685' are fluidly connected to second micropipette sample vessel 663, whose operation in this embodiment is essentially the same as described above with respect to first micropipette 665. An opening through second ball joint 671 allows second micropipette 667 to access the primary sample composition within primary sample chamber 651. Second micropipette 667 is sealed in a through passage of second ball joint 671 by seals 675 and 677, but second micropipette 667 is able to slide or otherwise move through seals 675 and 677. All of the openings in and out of containment vessel 650 comprise appropriate seals to ensure that the primary sample composition can be safely maintained under high-pressure, high-temperature conditions within primary sample chamber 651. Pressure inside primary sample chamber 651 is controlled using high-pressure positive displacement pumps (not illustrated) connected to the various flow lines, for example primary sample inlet and outlet (not illustrated in FIG. 6 but essentially the same as embodiment 100 in FIG. 2).

In embodiment 600, the sample probes are micropipette sampling tools 665 and 667, although other sample probes may be useful in practicing the invention, as further discussed herein. When micropipette sample probes are used, they comprise a hollow tube open on both ends, where one end, referred to herein as distal ends 696 and 696', may be tapered to a tip diameter on the order of tens of micrometers. During use, tapered distal ends 696 and 696' are located in primary chamber 651 with the tapered distal ends 696, 696' located in the space between sapphire windows 668 and 669 so that they may be viewed on the CCD camera 608. The middle portion of respective micropipettes 665, 667 extend through the center of joints 670, 671 which are also sealed as illustrated at 672, 673 and into respective pressure chambers 694, 695 defined by micropipette sample vessels 662, 663. Micropipettes 665, 667 may be formed from a single piece of metal, plastic, or glass, or may be formed from a composite of materials, such as a glass tube encased in metal or two metal tubes in a pipe-in-pipe configuration. Dynamic seals 674, 675, 676, and 677 surrounding micropipettes in joints 670, 671 act as explained previously with respect to embodiment 100 to isolate chamber primary chamber 651, and allow limited 3-dimensional movement of micropipettes 665, 667 as indicated by double-headed arrows 678, 679, 680, and 681. Micropipette sample vessels 662, 663 may be formed from a single piece of metal, including joints 670, 671 which may be ball joints, but need not be. The ball joint design allows movement of micropipette tips 696, 696' in 3-dimensions, where the center of the ball joint acts as the pivot point for radial and circular movement. The radial and circular movements allow micropipette distal ends 696, 696' to cover cone shaped spaces 83, as illustrated schematically in FIG. 4. The combined translational, radial, and circular movements allow for complete three-dimensional movement of at least the micropipette distal ends 696, 696' within primary chamber 651, and thus particles samples. Computer operated hydraulic or step gear motors (not illustrated) may be used to control the movements of micropipette distal ends 696, 696'. Fittings 682, 682' provide connections between solvent pumps 684, 684', and solvent supply lines 685, 685'. The ball mounted micropipette chambers 694, 695 may be filled with a carefully selected solvent during operation and the pressure of ball mounted micropipette chambers 694, 695 are balanced with the pressure in primary chamber 651.

FIG. 7 is a schematic cross section of another apparatus embodiment 700 of the invention that may be used to study rheological properties of particles and flocs. Embodiment 700 includes a body 750 forming a primary sample chamber 751 (inlet and outlet are similar to those of embodiment 100 discussed above and are not illustrated) along with sapphire windows 768 and 769. As illustrated in this embodiment, note that a sample isolated by distal end 796 of a first sample probe 765 is viewable by a microscope 708 (with the help of light source 709) the entire time it is present in primary sample chamber 751. A first hydraulic chamber 794 formed inside a first sample probe containment vessel 762 is connected to a first hydraulic pump 784. Similarly, a distal end 796' of a second sample probe 767 is viewable by microscope 708 (with the help of light source 709) the entire time it is present in primary sample chamber 751. A second hydraulic chamber 795 formed inside second sample probe containment vessel 763 is connected to a second hydraulic pump 785. Apparatus embodiment 700 differs from apparatus embodiment 600 in the operation of sample probes 765, 767. In embodiment 700, sample probes 765, 767 are supported in respective adjustment blocks 761, 759 each of which have a central passage through which the sample probe is inserted into and retracted from primary sample chamber 751 for the purpose of manipulating particles in primary sample chamber 751. Seals 772, 773, 776 and 777 prevent hydraulic fluid in chambers 794, 795 from entering primary sample chamber 751 and vice versa, and allow sample probes 765, 767, and thus distal ends 796, 796' to move in translational X-Y-Z directions, as indicated by the coordinate reference arrows.

Embodiments 200, 600, and 700 may include provisions for temperature control as explained in reference to embodiment 100. In all embodiments of the invention, a power source powers the light source, and may power a VCR and monitor or other viewing device.

Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention as defined in the following claims.

What is claimed is:

1. An apparatus comprising:
    (a) a primary sample containment vessel defining a primary chamber, the containment vessel having walls comprising materials capable of maintaining temperatures and pressures in the primary chamber at least different than ambient conditions, and further comprising two or more viewing ports comprising materials selected from natural and synthetic materials having optical and mechanical properties suitable for high-pressure, high-temperature applications, the primary chamber having a primary sample inlet and outlet;
    (b) a secondary sample collection container defining a collection chamber fluidly connected to the primary containment vessel;
    (c) a sample probe comprising a distal end able to isolate a secondary sample in the primary chamber and transfer the secondary sample to the collection chamber, the sample probe fluidly connected to the primary chamber via a seal between the containment vessel and the sample probe allowing 3-dimensional movement of at least the distal end of the sample probe within the primary chamber; and
    (d) a camera or other charge couple device positioned to visually access the primary chamber through one viewing port, and a light source visually connected to a second viewing port and allowing light from the light source to enter the primary chamber.

2. The apparatus of claim 1 wherein the materials of the viewing ports are selected from sapphire and quartz.

3. The apparatus of claim 1 wherein the sample probe is selected from solid and hollow objects.

4. The apparatus of claim 3 wherein the sample probe is selected from a pointed object, a cup-shaped object, a catheter-like device comprising a sample grabber, and a pipette.

5. An apparatus comprising:
    (a) a primary sample containment vessel defining a primary chamber, the containment vessel having walls comprising materials capable of maintaining temperatures and pressures in the primary chamber at least different than ambient conditions, the primary chamber having a primary sample inlet and outlet;
    (b) a secondary sample collection container defining a collection chamber fluidly connected to the primary containment vessel; and
    (c) a sample probe comprising a distal end able to isolate a secondary sample in the primary chamber and transfer the secondary sample to the collection chamber, the sample probe fluidly connected to the primary chamber via a seal between the containment vessel and the sample probe allowing 3-dimensional movement of at least the distal end of the sample probe within the primary chamber, and
    wherein the primary containment vessel and the secondary sample collection container are fluidly connected by a barrier selected from mechanical barriers, interfacial barriers and any other form of barrier preventing the secondary sample collection chamber being contaminated by non-sampled material in the primary chamber.

6. The apparatus of claim 5 wherein if the barrier is a mechanical barrier it is selected from elastomeric membrane materials, and if the barrier is an interfacial barrier it is selected from an interface between two immiscible fluids.

7. An apparatus comprising:
    (a) a primary sample containment vessel defining a primary chamber, the containment vessel having walls comprising materials capable of maintaining temperatures and pressures in the primary chamber at least different than ambient conditions, the primary chamber having a primary sample inlet and outlet;
    (b) a secondary sample collection container defining a collection chamber fluidly connected to the primary containment vessel; and
    (c) a sample probe comprising a distal end able to isolate a secondary sample in the primary chamber and transfer the secondary sample to the collection chamber, the sample probe fluidly connected to the primary chamber via a seal between the containment vessel and the sample probe allowing 3-dimensional movement of at least the distal end of the sample probe within the primary chamber, and
    wherein the secondary sample collection container comprises an internal floating piston which functions to allow secondary samples to fill a sub-chamber of the sample collection container, the floating piston fluidly connected to a system allowing two-way flow of a motive fluid to effect and/or allow movement of the floating piston.

8. An apparatus comprising:
    (a) a primary sample containment vessel defining a primary chamber, the containment vessel having walls comprising materials capable of maintaining temperatures and pressures in the primary chamber at least different than ambient conditions, the primary chamber having a primary sample inlet and outlet;

(b) a secondary sample collection container defining a collection chamber fluidly connected to the primary containment vessel; and (c) a sample probe comprising a distal end able to isolate a secondary sample in the primary chamber and transfer the secondary sample to the collection chamber, the sample probe fluidly connected to the primary chamber via a seal between the sample probe and the containment vessel allowing 3-dimensional movement of at least the distal end of the sample probe within the primary chamber, wherein the seal between the sample probe and the containment vessel comprises a joint having a substantially central passage therethrough, wherein the sample probe is positioned and sealed in the central passage, wherein the joint is an integral component of a pressurized sample probe container defining a sample probe chamber, wherein the joint allows 3-dimensional movement of at least the distal end of the sample probe within the primary chamber, and translational movement of the sample probe in and out of the collection chamber and sample probe chamber, and wherein the sample probe is a micropipette, and the micropipette and sample probe chamber are fluidly connected to a system allowing two-way flow of a solvent to effect suction and pressurization of the micropipette.

9. The apparatus of claim 8 wherein the distal end of the micropipette is able to isolate secondary samples having a largest length dimension of no larger than about 1 micrometer.

10. The apparatus of claim 1 wherein the containment vessel walls comprise materials capable of maintaining temperatures and pressures in the primary chamber representative of a hydrocarbon-bearing reservoir.

* * * * *